United States Patent
Chevalier et al.

(10) Patent No.: US 7,056,498 B2
(45) Date of Patent: Jun. 6, 2006

(54) COMPOSITION CONTAINING AMINOPHENOL DERIVATIVE, USE THEREOF, AND PROCESS FOR DISSOLVING AMINOPHENOL DERIVATIVE

(75) Inventors: Veronique Chevalier, Villecresnes (FR); Melanie Quest, Paris (FR)

(73) Assignee: L'Oreal, Paris (FR)

( * ) Notice: Subject to any disclaimer, the term of this patent is extended or adjusted under 35 U.S.C. 154(b) by 202 days.

(21) Appl. No.: 09/739,873

(22) Filed: Dec. 20, 2000

(65) Prior Publication Data

US 2002/0026068 A1    Feb. 28, 2002

(30) Foreign Application Priority Data

Dec. 20, 1999    (FR) .................................. 99 16075

(51) Int. Cl.
*A61K 7/021*    (2006.01)
*A61K 31/74*    (2006.01)
*A61K 31/135*   (2006.01)

(52) U.S. Cl. ................. 424/63; 424/78.02; 424/78.03; 514/651; 514/652

(58) Field of Classification Search ................ 514/844, 514/587, 651, 652; 424/63, 78.02, 78.03; 8/412

See application file for complete search history.

(56) References Cited

U.S. PATENT DOCUMENTS

| | | | | |
|---|---|---|---|---|
| 4,330,292 | A | * | 5/1982 | Bugaut et al. |
| 4,888,025 | A | * | 12/1989 | Bugaut et al. |
| 4,948,843 | A | * | 8/1990 | Roberts et al. .......... 525/328.2 |
| 5,453,498 | A | * | 9/1995 | Nakamura et al. .......... 536/119 |
| 5,559,110 | A | * | 9/1996 | Aungst ........................ 514/218 |
| 5,580,357 | A | * | 12/1996 | Cotteret et al. |
| 5,789,521 | A | * | 8/1998 | Marrocco et al. .......... 528/125 |
| 5,945,395 | A | * | 8/1999 | Yamashita et al. .......... 510/444 |
| 5,955,091 | A | * | 9/1999 | Hansenne |
| 5,961,666 | A | * | 10/1999 | Lim et al. |
| 6,159,482 | A | | 12/2000 | Tuloup et al. |
| 6,203,781 | B1 | * | 3/2001 | Chevalier et al. |
| 6,423,854 | B1 | | 7/2002 | Philippe et al. |
| 6,582,734 | B1 | * | 6/2003 | Wei et al. ................... 424/665 |
| 2002/0142017 | A1 | | 10/2002 | Simonnet |
| 2002/0161040 | A1 | | 10/2002 | Phillippe et al. |

FOREIGN PATENT DOCUMENTS

| | | | |
|---|---|---|---|
| EP | 0 709 225 | | 5/1996 |
| EP | 0 898 956 | | 3/1999 |
| EP | 0962224 | * | 5/1999 |
| FR | 2796838 | | 7/1999 |
| FR | 2 778 561 | | 11/1999 |
| GB | 1 349 955 | | 4/1974 |
| JP | 61227516 | | 10/1985 |
| JP | 6-344672 | | 12/1994 |
| JP | 7-22366 | | 8/1995 |
| JP | 09077655 | * | 3/1997 |
| WO | WO98/03150 | * | 1/1998 |
| WO | WO 98/07406 | | 2/1998 |
| WO | WO 99/10318 | * | 3/1999 |

OTHER PUBLICATIONS

Zhang et al., Miscellar solubilization . . . , Database Caplus, AN1999:415428, Qingdao Huagong Xueyuan Xuebao, 1998, vol. 19(2), pp. 110-115.*

Patent Abstracts of Japan; vol. 1995, No. 06, Jul. 7, 1995, & JP 07061905, Mar. 7, 1995.

K. Sakuma et al, "Relationship Between Tyrosinase Inhibitory Action and Oxidation-Reduction Potential of Cosmetic Whitening Ingredients and Pheno Derivatives"; Arch Pharm Res; vol. 22, No. 4, pp. 335-339; 1999, XP000882119.

Database WPI, Week 9722, Derwent Publications Ltd, London, GB; AN 1997-241638; XP-002086051.

Bellstein Records, 3183408, STN Abstract, 1991.

* cited by examiner

*Primary Examiner*—Vickie Kim
(74) *Attorney, Agent, or Firm*—Oblon, Spivak, McClelland, Maier & Neustadt, P.C.

(57) ABSTRACT

Composition containing at least one aminophenol derivative and a solubilizing compound which is not in the form of vesicles, chosen from: (a) oxyalkylenated fatty acid esters of sorbitan, (b) oxyalkylenated hydrogenated castor oils, and/or (c) oxyalkylenated fatty alcohols. The invention also relates to a process for dissolving at least one aminophenol derivative by mixing it with a solubilizing agent as defined above.

18 Claims, No Drawings

COMPOSITION CONTAINING AMINOPHENOL DERIVATIVE, USE THEREOF, AND PROCESS FOR DISSOLVING AMINOPHENOL DERIVATIVE

BACKGROUND OF THE INVENTION

1. Field of the Invention

The invention relates to a composition, in a particular embodiment to a cosmetic composition, comprising an aminophenol derivative, as well as to the uses thereof. The invention also relates to a process for dissolving an aminophenol derivative.

2. Background

For several years, considerable effort has been devoted to proposing harmless topical depigmenting substances that show good efficacy.

These substances are particularly sought in order to treat regional hyperpigmentations caused by melanocyte hyperactivity, such as idiopathic melasmas, occurring during pregnancy ("pregnancy mask" or chloasma) or during oestro-progestative contraception, localized hyperpigmentations caused by hyperactivity and proliferation of benign melanocytes, such as senile pigmentation marks known as actinic lentigo, accidental hyperpigmentations or depigmentations, possibly due to light-induced sensitization or to post-lesional cicatrization, as well as certain leukodermas, such as vitiligo. For the latter (in which the cicatrizations can result in a scar which gives the skin a whiter appearance and leukodermas), failing the ability to repigment the damaged skin, the regions of residual normal skin are depigmented in order to give the skin an overall uniform white complexion.

Various depigmenting agents have been proposed in the prior art. In particular, it has been demonstrated that certain aminophenol derivatives have the ability to inhibit melanogenesis, even at low concentrations, without showing any cytotoxicity. These compounds, as well as the method for preparing them, are disclosed in patent application WO 99/10318 and are aminophenols containing a relatively long or short hydrocarbon-based chain, preferably an alkoxycarbonyl chain, linked to the nitrogen atom. They have the drawback of being only sparingly or not at all soluble in water. For the short-chain hydrocarbon-based compounds, their introduction into cosmetic compositions requires a dissolution in aqueous-alcoholic solution, which is not always desirable when the composition is intended, for example, to be applied to the area around the eyes. In addition, it has been noted that aqueous-alcoholic gels have a tendency to trap these compounds in their network, thus limiting their diffusion into the malpighian epidermis.

As regards the long-chain hydrocarbon-based compounds, they are insoluble in oils, on account of their stearic bulk, and have a tendency to recrystallize in water. In patent application FR-99/09663, it has been proposed to incorporate them into the bilayer of lipid vesicles in order to facilitate their formulation in cosmetic products. However, this inclusion involves an implementation which is occasionally intricate.

It thus remains necessary to be able to dissolve these aminophenol derivatives readily in a physiologically acceptable medium which entails a minimum of discomfort when applied to the skin or the scalp, and which is easy to use. In addition, it is necessary to be able to dissolve an amount of these compounds which is sufficient for cosmetic or dermatological use, without recrystallization of these compounds or loss of stability of the composition containing them. The reason for this is that this instability would result in a greater or smaller loss of efficacy of these compositions and/or in a change in their appearance, which would run the risk of putting users off using them.

SUMMARY OF THE INVENTION

However, the inventors have now discovered that these and other aminophenol derivatives can be dissolved in certain oxyalkylenated fatty acid esters of polyols and/or in oxyalkylenated fatty alcohols.

A subject of the present invention is thus a composition comprising, preferably in a physiologically acceptable form or medium, at least one solubilizing compound which is not in or in the form of vesicles, chosen from:

(a) oxyalkylenated fatty acid esters of sorbitan,
(b) oxyalkylenated hydrogenated castor oils, and/or
(c) oxyalkylenated fatty alcohols,
and at least one aminophenol derivative of formula:

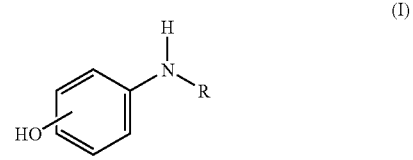

in which R is chosen from a radical of formula (a), (b) or (c) below:
(a) —CO—NR$_1$R$_2$
(b) —CO—O—R$_3$
(c) —SO$_2$—R$_3$
in which:

R$_1$ represents a hydrogen atom or a linear or branched, saturated or unsaturated, optionally hydroxylated C$_1$–C$_6$ alkyl radical, R$_2$ represents a hydrogen atom or a radical chosen from a saturated or unsaturated, linear, cyclic or branched, optionally hydroxylated C$_1$–C$_{30}$ alkyl radical, and R$_3$ represents a radical chosen from a saturated or unsaturated, linear, cyclic or branched, optionally hydroxylated C$_1$–C$_{30}$ alkyl radical.

R$_1$, R$_2$ and R$_3$, when hydroxylated preferably contain from 1–5 —OH groups. In one preferred embodiment the aminophenol derivative is not in nor in the form of a vesicle.

A subject of the invention is also a process for dissolving at least one aminophenol derivative of formula (I) above, comprising contacting, mixing, etc., it with at least one solubilizing agent as defined above.

DETAILED DESCRIPTION OF THE INVENTION

Derivatives of formula (I) above, as well as a process for preparing them, are disclosed in patent application WO 99/10318, which is incorporated herein by reference. Such derivatives may be made by those of skill in the art, and in particular comprise para-aminophenol derivatives, preferred examples of which are N-cholesteryloxycarbonyl-4-para-aminophenol and N-ethyloxycarbonyl-4-para-aminophenol.

The oxyalkylenated fatty acid esters of sorbitan which can be used according to the invention are not particularly limited, however, preferred ones include oxyethylenated sorbitan monoesters, preferably formed from a saturated fatty acid containing from 8 to 30 carbon atoms, including 10, 15, 20 and 25, such as oxyethylenated (20 EO) sorbitan monostearate and oxyethylenated (20 EO) sorbitan monolaurate.

The oxyalkylenated hydrogenated castor oils which can be used according to the invention are not particularly limited, however, preferred ones include oxyethylenated hydrogenated castor oils containing, for example, from 7 to 60 ethylene oxide units, preferably from 40 to 60 ethylene oxide units, including 45, 50 and 55 ethylene oxide units.

Fatty alcohols which can be used according to the invention are not particularly limited, however, preferred ones include oxyethylenated and/or oxypropylenated fatty alcohols, which are preferably saturated, the hydrocarbon-containing chain of which advantageously containing from 8 to 30 carbon atoms, including 10, 15, 20 and 25. Examples of oxyalkylenated fatty alcohols include oxyethylenated (20 EO) oxypropylenated (5 PO) cetyl alcohol, oxyethylenated lauryl alcohol comprising 4 or 23 ethylene oxide units and the mixture of oxyethylenated cetyl and stearyl alcohols, comprising 20 ethylene oxide units.

The solubilizing compound can be used alone or in combination with one or more of any other solubilizing compound (a), (b), or (c). Of course, more than one compound from each of (a), (b) and (c) may be used in combination also. Thus, a composition according to the invention may include two compounds from (b) and one from (c), for example. Also, more than one compound of formula I may be present.

These solubilizing compounds are oxyalkylenated, i.e. generally oxyethylenated and/or oxypropylenated. The reason for this is that it has been found that these solubilizing agents make it possible, surprisingly, to dissolve an amount of aminophenol derivative at least equal to 10% by weight, relative to the total weight of the solubilizing agent used, at a temperature generally below 80° C., without resulting in any recrystallization of the aminophenol derivative at room temperature.

The solubilizing agents defined above can be used to dissolve the aminophenol derivative of formula (I) before introducing it, for example, either into an oily phase or into an aqueous phase of, e.g., a cosmetic composition.

Invention compositions may contain only the above solubilizing compound(s) and one or more compounds of formula I, and can also contain in addition other components. Preferred compositions contain from 0.01% to 15% by weight including 0.1, 0.5, 1, 2, 3, 4, 5, 6, 7, 8, 9, 10, 11, 12, 13 and 14% and preferably from 0.5% to 5% by weight of aminophenol derivative relative to the total weight of the composition. The amount of solubilizing agent will depend on the amount of aminophenol derivative to be dissolved and may range, for example, from 0.05% to 25% by weight including 0.1, 0.5, 1, 3, 5, 7, 9, 11, 13, 15, 17, 19, 21 and 23% and preferably from 2% to 20% by weight relative to the total weight of the composition.

When only solubilizing compound(s) and compound(s) of Formula I are present in composition the amount of solubilizing compound(s) may be from 50–99+wt % including 99.99 wt % with the remainder compound(s) of Formula I.

Compositions according to the invention are useful for topical application to the skin or the hair and thus preferably comprise a physiologically acceptable medium, i.e. a medium which is compatible with the skin and/or its superficial growths (nails, body hairs, head hair).

The composition can be in any pharmaceutical form normally used for topical application, in particular in the form of an aqueous or aqueous alcoholic solution, an oil-in-water or water-in-oil or multiple emulsion, an aqueous or oily gel, or an anhydrous liquid, pasty or solid product.

This composition can be more or less fluid and can have the appearance of a white or coloured cream, an ointment, a milk, a lotion, a serum, a paste or a mousse. It may optionally be applied to the skin or to the hair in aerosol form. It may also be in solid form and, for example, in the form of a stick. In a known manner, the composition according to the invention can also contain the usual adjuvants in the cosmetics and dermatological fields, such as hydrophilic or lipophilic gelling agents, hydrophilic or lipophilic active agents, preserving agents, antioxidants, solvents, fragrances, fillers, screening agents, pigments, odour absorbers and dyestuffs. The amounts of these various adjuvants are those conventionally used in the fields under consideration, and, for example, from 0.01% to 20% of the total weight of the composition. Depending on their nature, these adjuvants can be introduced into the fatty phase, into the aqueous phase, into lipid vesicles and/or into nanoparticles.

It is within the skill of a person skilled in the art to select these optional additional active or inactive compounds, and/or the amount thereof, preferably such that the advantageous properties of the aminophenol derivatives are not, or are not substantially, adversely affected by the addition.

When the composition according to the invention is an emulsion, the proportion of the fatty phase is not limited and can range from 0.5% to 80% by weight and preferably from 5% to 50% by weight relative to the total weight of the composition. The oils, emulsifiers and coemulsifiers used in the composition in emulsion form are chosen from those used conventionally in the field considered.

As oils which can be used in the invention, examples include mineral oils (liquid petroleum jelly), oils of plant origin (avocado oil, soybean oil), oils of animal origin (lanolin), synthetic oils (perhydrosqualene), silicone oils (cyclomethicone) and fluoro oils (perfluoropolyethers). Fatty alcohols (cetyl alcohol), fatty acids and waxes (carnauba wax, ozokerite) can also be used as fatty substances.

As emulsifiers and coemulsifiers which can be used in the invention, examples include, for example, in addition to the agent for dissolving the aminophenol derivative, of fatty acid esters of polyethylene glycol such as PEG-20 stearate, and fatty acid esters of glycerol such as glycerol stearate.

As hydrophilic gelling agents, examples include in particular carboxyvinyl polymers (carbomer), acrylic copolymers such as acrylate/alkylacrylate copolymers, polyacrylamides, polysaccharides, natural gums and clays, and, as lipophilic gelling agents, mention may be made of modified clays such as bentones, metal salts of fatty acids, hydrophobic silica and polyethylenes.

Keratolytic and/or desquamating agents, UV screening agents, anti-irritants and calmants and mixtures thereof may be used in particular as active agents. In addition, although the aminophenol derivative(s) has by itself a depigmenting activity which justifies its use as sole depigmenting active agent for a bleaching composition, other depigmenting agents may also be added to the composition according to the invention, thus allowing them to be used in lower doses. In the event of incompatibility, at least some of the active agents can be incorporated into spherules, in particular ionic or nonionic vesicles and/or nanoparticles (nanocapsules and/or nanospheres), such that the active agents that are incompatible with each other or with the aminophenol derivatives are isolated from one another in the composition.

Composition(s) according to the invention can in particular constitute protective, care or make-up products for the face, for the neck, for the hands or for the body. As a variant, it can be in the form of a hair product, in particular a shampoo or a conditioner. This composition is particularly suitable for topical use, in order to bleach and/or depigment the skin, body hairs and/or head hair.

The present invention thus relates also to a cosmetic process for depigmenting and/or bleaching human skin, body hairs and/or head hair, characterized by applying a composition as described above to the skin, body hairs and/or head hair.

Lastly, the present invention relates to the use of the composition defined above to manufacture a preparation intended for depigmenting and/or bleaching the skin, body hairs and/or head hair.

The invention will now be illustrated with the aid of the non-limiting examples which follow. Except where otherwise indicated, the amounts are given as percentages by weight.

EXAMPLE 1

Fluid Emulsion

The following composition was prepared.

| Phase A | |
|---|---|
| N-ethyloxycarbonyl-4-para-aminophenol | 0.5% |
| mixture of oxyethylenated (20 EO) cetyl and stearyl alcohols | 2% |
| oxyethylenated (60 EO) hydrogenated castor oil | 2.5% |
| Phase A' | |
| apricot oil | 5 |
| UV screening agents | 3.9% |
| cyclohexasiloxane | 10% |
| polyethoxylated (20 EO) methylglucose sesquistearate | 2% |
| Phase B | |
| preserving agents | 0.65% |
| triethanolamine | 0.5% |
| disodium EDTA | 0.05% |
| glycerol | 5% |
| demineralized water qs | 100% |
| Phase C | |
| gelling agents | 4.25% |

The composition was prepared in the following way: phase A was heated to about 80° C. until dissolution was complete, and then introduced into phase B which had been preheated to the same temperature. Phase A' was heated to about 80° C. and then introduced into the mixture previously obtained, to form an O/W emulsion into which phase C was then added at a temperature of about 50° C.

This composition makes it possible to fade out pigmentation marks on the face, the neckline and the hands.

After storage for two months at room temperature and at 45° C., no change in the viscosity or colour of the composition and no release of odour were observed. In addition, no decrease was found in the N-ethyloxycarbonyl-4-para-aminophenol content, as determined by HPLC, and no formation of crystals of this compound was observed.

EXAMPLE 2

Fluid Emulsion

| Phase A | |
|---|---|
| N-cholesteryloxycarbonyl-4-para-aminophenol | 0.5% |
| mixture of oxyethylenated (20 EO) cetyl and stearyl alcohols | 2% |
| oxyethylenated (60 EO) hydrogenated castor oil | 2.5% |
| Phase A' | |
| apricot oil | 5% |
| UV screening agents | 5.6% |
| cyclohexasiloxane | 5% |
| polyethoxylated (20 EO) methylglucose sesquistearate | 2% |
| methylglucose sesquistearate | 2% |
| Phase B | |
| preserving agents | 0.65% |
| triethanolamine | 1.35% |
| disodium EDTA | 0.05% |
| glycerol | 3% |
| demineralized water qs | 100% |
| Phase C | |
| gelling agents | 2.25% |

This composition was prepared in the following way: phase A was first heated to about 80° C. until dissolution is complete, and was then introduced into phase A' which had been preheated to the same temperature. The mixture was then added to phase B which was heated to about 80° C. for emulsification, after which phase C was incorporated at about 50° C. into the O/W emulsion thus obtained.

This composition makes it possible to fade out pigmentation marks on the face, the neckline and the hands.

After storage for two months at room temperature and at 45° C., no change in the viscosity or colour of the composition and no release of odour were observed. In addition, no decrease was found in the N-cholesteryloxycarbonyl-4-para-aminophenol content, as determined by HPLC, and no formation of crystals of this compound was observed.

EXAMPLE 3

Bleaching Fluid

| Phase A | |
|---|---|
| N-cholesteryloxycarbonyl-4-para-aminophenol | 0.5% |
| plant oils | 13% |
| W screening agents | 6% |
| cyclopentasiloxane | 7% |
| oxyethylenated (60 EO) hydrogenated castor oil | 2.5% |
| Phase B | |
| preserving agents | 0.3% |
| disodium EDTA | 0.05% |
| isophthalate/sulphoisophthalate/dimethylol cyclohexane/diethylene glycol copolymer (Eastman AQ 38S from Eastman Chem. Co.) | 2% |
| glycerol | 5% |
| demineralized water qs | 100% |

This fluid makes it possible to fade out pigmentation marks on the face, the neckline and the hands.

The composition was obtained in the following way: phases A and B were heated separately to 80° C. and then cooled to room temperature. Phase B was then introduced into phase A in order to obtain an W/O emulsion which was then passed through a high-pressure homogenizer.

After storage for two months at room temperature and at 45° C., no change in the viscosity or colour of the composition and no release of odour were observed. In addition, no decrease was found in the N-cholesteryloxycarbonyl-4-para-aminophenol content, as determined by HPLC, and no formation of crystals of this compound was observed.

EXAMPLE 4

Comparison of the Solubilizing Agents

The amount of aminophenol derivative (N-ethyloxyearbonyl-4-para-aminophenol, or EPAP, and N-cholesteryloxyyearbonyl-4-para-aminophenol, or CPAP) which can be dissolved in various solubilizing agents, at 60° C., was compared in Tables 1 and 2 below.

TABLE 1

Dissolution of EPAP and CPAP with esters

| Solubilizing agent | Amount of EPAP dissolved | Amount of CPAP dissolved |
|---|---|---|
| Oxyethylenated (20 EO) sorbitan monostearate | 50% | 14.2% |
| Oxyethylenated (7 EO) hydrogenated castor oil | 16.6% | 12.5% |
| Oxyethylenated (40 EO) hydrogenated castor oil | 16.5% | 16.5% |
| Oxyethylenated (60 EO) hydrogenated castor oil | 16.5% | 16.5% |
| Apricot kernel oil | insoluble | insoluble |
| Mineral oil | insoluble | insoluble |
| Caprylic/capric triglycerides | 4.7% (80° C.); recrystallizes at room temperature | 0.5% |

It emerges clearly from Table 1 above that the non-oxyalkylenated oils and fatty acid esters do not make it possible to dissolve, or only sparingly dissolve, the aminophenol derivatives according to the invention.

TABLE 2

Dissolution of EPAP and CPAP with alcohols

| Solubilizing agent | Amount of EPAP dissolved | Amount of CPAP dissolved |
|---|---|---|
| Laureth-23 | not tested | 4.8% |
| Laureth-4 | 25% | 4.8% |
| Oxyethylenated (20 EO) oxypropylenated (5 PO) cetyl alcohol | 16.5% | 14.2% |
| Octyldodecanol | insoluble | 0.5% |
| Hexyldecanol | insoluble | insoluble |

It emerges from Table 2 above that the nonoxyalkylenated fatty alcohols do not make it possible to dissolve, or only sparingly dissolve, the aminophenol derivatives according to the invention.

It has also been observed that a mixture of oxyethylenated (26 EO) oxypropylenated (26 PO) butyl alcohol and oxyethylenated (40 EO) hydrogenated castor oil makes it possible to dissolve 20% of EPAP and 14.2% of CPAP and that the mixture of oxyethylenated (9 EO) tridecyl alcohol and of oxyethylenated (40 EO) hydrogenated castor oil makes it possible to dissolve 25% of EPAP.

French patent application 9916075 filed Dec. 20, 1999, is incorporated herein by reference.

What is claimed is:

1. A composition comprising A.) an N-cholesteryloxycarbonyl-4-para-aminophenol solubilizing effective amount of a solubilizing compound selected from the group consisting of:
   (a) oxyalkylenated fatty acid esters of sorbitan,
   (b) oxyalkylenated hydrogenated castor oils, and
   (c) oxyalkylenated fatty alcohols,
   and B.) the aminophenol derivative N-cholesteryloxycarbonyl-4-para-aminophenol.

2. A composition according to claim 1, wherein the total amount of said aminophenol derivative represents from 0.01% to 15% by weight relative to the total weight of the composition.

3. A composition according to claim 1, wherein said solubilizing compound is selected from oxyethylenated hydrogenated castor oils, oxyethylenated sorbitan monoesters, and oxyethylenated and/or oxypropylenated fatty alcohols.

4. A composition according to claim 1, wherein said solubilizing compound represents from 0.05% to 25% by weight relative to the total weight of the composition.

5. A composition as claimed in claim 4, comprising 2–20% by weight solubilizing compound.

6. A composition as claimed in claim 2, comprising 0.5–5% by weight aminophenol derivative.

7. A process for depigmenting and/or bleaching human skin, body hairs and/or head hair, comprising applying a composition according to claim 1 to the skin, body hairs and/or head hair.

8. A composition according to claim 1, wherein said solubilizing compound is an oxyalkylenated fatty acid ester of sorbitan.

9. A composition according to claim 1, wherein said solubilizing compound is an oxyalkylenated hydrogenated castor oil.

10. A composition according to claim 1, wherein said solubilizing compound is an oxyalkylenated fatty alcohol.

11. A composition according to claim 4, comprising 2–5% by weight solubilizing compound.

12. A composition according to claim 1, wherein said solubilizing compound contains from 20 to 60 ethylene oxide units.

13. A composition comprising an N-cholesteryloxycarbonyl-4-para-aminophenol solubilizing effective amount of an oxyalkylenated fatty alcohol and N-cholesteryloxycarbonyl-4-para-aminophenol.

14. The composition of claim 13, wherein the hydrocarbon containing chain of the oxyalkylenated fatty alcohol contains 8 to 30 carbon atoms.

15. The composition of claim 13, wherein the hydrocarbon containing chain of the oxyalkylenated fatty alcohol contains 10 to 20 carbon atoms.

16. The composition of claim 13, wherein the oxyalkylenated fatty alcohol contains 4 to 23 alkylene oxide units.

17. The composition of claim 14, wherein the oxyalkylenated fatty alcohol contains 4 to 23 alkylene oxide units.

18. The composition of claim 15, wherein the oxyalkylenated fatty alcohol contains 4 to 23 alkylene oxide units.

* * * * *